United States Patent
Flamer (10) Patent No.: US 6,451,257 B1
(45) Date of Patent: Sep. 17, 2002

(54) ARTERIAL BLOOD FILTER

(75) Inventor: Denise R. Flamer, Newark, DE (US)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/398,005

(22) Filed: Sep. 16, 1999

(51) Int. Cl.[7] .................................................. A61M 1/36
(52) U.S. Cl. .......................... 422/44; 210/436; 210/456; 210/472
(58) Field of Search .................. 210/407, 416.1, 210/419, 420, 436, 437, 439, 472, 451, 452; 604/6.09, 333, 405, 406; 422/44–45

(56) References Cited

U.S. PATENT DOCUMENTS

| | | | |
|---|---|---|---|
| 3,359,708 A | | 12/1967 | Barber |
| 3,771,290 A | | 11/1973 | Stethem |
| 3,827,562 A | | 8/1974 | Esmond |
| 3,996,027 A | | 12/1976 | Schnell et al. |
| 4,344,777 A | | 8/1982 | Siposs |
| 4,345,919 A | | 8/1982 | Wilkinson et al. |
| 4,411,783 A | | 10/1983 | Dickens et al. |
| 4,490,254 A | * | 12/1984 | Gordon et al. ............... 210/247 |
| RE32,711 E | * | 7/1988 | Dickens et al. ............. 210/304 |
| 4,806,135 A | | 2/1989 | Siposs |
| 4,824,567 A | * | 4/1989 | Turman .................... 210/416.4 |
| 4,919,802 A | | 4/1990 | Katsura |
| 5,158,533 A | * | 10/1992 | Strauss et al. ............... 210/436 |
| 5,196,119 A | * | 3/1993 | Harms et al. ............... 210/438 |
| 5,312,479 A | | 5/1994 | Weinstein et al. |
| 5,462,675 A | | 10/1995 | Hopkins et al. |
| 5,601,710 A | * | 2/1997 | Yoon et al. .................. 210/232 |
| 5,618,425 A | | 4/1997 | Mitamura et al. |
| 6,176,903 B1 | * | 1/2001 | Wamsiedler ................. 210/436 |
| 6,302,860 B1 | * | 10/2001 | Gremel et al. .............. 210/436 |

FOREIGN PATENT DOCUMENTS

EP     1084722     *  9/2000

* cited by examiner

Primary Examiner—Angela D. Sykes
Assistant Examiner—Leslie R. Deak
(74) Attorney, Agent, or Firm—Burns, Doane, Swecker & Mathis, LLP (57) ABSTRACT

An arterial blood filter device for use during cardiovascular surgery. The device includes an outer housing having a top and bottom section, an inner housing, and a filter element. The filter element is disposed within the outer housing, and the inner housing is disposed between the filter element and the housing. The inner housing is separate from the outer housing and extends the entire axial length of the filter element. Fluid enters the device through an inlet. The majority of the fluid then rises in a centripetal motion where any large air bubbles exit through a vent at the top section of the outer housing. The fluid then flows through openings in the top and bottom of the inner housing. After entering the inner housing, the fluid passes through a filter element, where filtration takes place, and exits through the bottom section of the housing through an outlet.

30 Claims, 5 Drawing Sheets

ARTERIAL BLOOD FILTER

FIELD OF THE INVENTION

The present invention generally relates to an arterial blood filter. More particularly, the present invention pertains to an arterial blood filter used in an extracorporeal circuit during cardiovascular surgery.

BACKGROUND OF THE INVENTION

During cardiovascular surgery, the patient's blood is circulated via an extracorporeal circuit. The patient's blood exits the body via a venous cannula, which is a flexible tube that is inserted over a vein. The venous cannula is placed either in the superior or inferior vena cava, which are veins that drain blood from the upper body and the lower body and empty into the right atrium of the heart.

Typically, the blood from the body enters a reservoir and is then pumped through an oxygenator with an incorporated heat exchanger. After passing through the oxygenator, the blood enters an arterial filter. The arterial filter is designed to remove air, debris, and aggregated blood elements, and is usually the last component in the circuit through which the blood passes before being returned to the patient. The blood is then returned to the patient via an arterial cannula which is placed in the aorta, and then circulated throughout the patient's body.

A blood filter should be designed to have low resistance to flow, small priming volume and smooth inside surfaces, and should avoid traumatizing formed blood elements. More importantly, the filter must be able to assist in the removal of air and other undesirable constituents prior to being returned to the patient.

Typically, arterial filters generally consist of a top housing, a bottom housing, and a filter element, and sometimes a cap to hold the filter element in place. However, there are many disadvantages associated with these known filtering devices.

For instance, U.S. Pat. No. 3,827,562 to Esmond discloses a device for the removal of gases, particulate matter and oil primarily from blood after the treatment of the blood in an artificial body device. The filter device utilizes a plurality of filter cloth layers disposed generally parallel to the path of blood flow and supported against collapse by a relatively coarse mesh disposed between adjacent filter cloth layers. The filter layers are disposed in the bottom portion of the housing and completely fill the bottom portion, so that there is no space between the bottom portion of the housing and the filter layers.

The blood enters through an inlet conduit disposed on the side of the housing, with an exit conduit disposed at the bottom portion of the housing and an air conduit located in the top portion of the housing. As the blood enters the device, the blood rests on the top of the filter layers, and eventually sinks through the filter layers, thereby entrapping gases or bubbles contained in the blood. However, the blood that accumulates adjacent the filter cloth is not sufficiently exposed to the air conduit for venting. The blood accumulated adjacent to the filter cloth travels too rapidly through the filter cloth, and hence does not have sufficient exposure to the air vent for removal of air bubbles.

U.S. Pat. No. 4,411,783 to Dickens et al. discloses a blood filter including a filter element comprising an array of layers. The filter element is disposed within a housing and includes a perforated tubular core at its center, and a filter cap covering the upper ends of the core and the filter element. Blood enters the blood filter from a blood inlet tangentially disposed at the top portion of the housing, and flows in a swirling motion outside the filter element and above the filter element cap. However, because of the swirling motion, blood enters the filter element along its outer surface and at too high a rate of speed, which prevents proper air removal.

U.S. Pat. No. 4,919,802 to Katsura discloses a blood filter having a bubble separating section including a generally cylindrical chamber for allowing the bubbles to separate from blood, an air discharging vent at an upper end of the chamber, and an inlet conduit horizontally extending from the chamber for introducing blood into the chamber. However, because the blood is centripetally directed about the filter element, the fluid comes in direct contact with the filter element at high shear rates, and is discharged too rapidly from the filter without subjecting the blood to sufficient air removal.

U.S. Pat. No. 4,490,254 to Gordon et al. relates to a blood filter assembly in which blood enters at the bottom end of the assembly, is directed in a spirally upward path and then passes through a filter medium. After passing through the filter medium, the blood flows downwardly out of an outlet in the bottom end of the assembly. A gas vent is provided at the top end of the assembly for air removal. However, because the blood is centripetally directed about the filter element, the fluid comes in direct contact with the filter element at high shear rates, and is discharged too rapidly from the filter without subjecting the blood to sufficient air removal.

U.S. Pat. No. 4,344,777 to Siposs discloses an arterial blood filter having an internal divergent blood flow path from the inlet to smoothly reduce blood flow velocity and permit separation of air bubbles with minimum trauma to blood cells. The blood is received into the flow cone and the blood flows over the cone and into the filter element. A shield is formed as part of the flow cone, and extends part of the length of the filter element. The shield functions to lengthen the path the air bubbles have to travel before they reach the filter element. However, the blood must travel through complicated paths, potentially disrupting or damaging fragile blood cells.

U.S. Pat. No. 5,462,675 to Hopkins et al. discloses a filter assembly for decreasing fluid hold-up waste and providing uniform flow while maintaining desired flow rates and pressures. The assembly includes a housing, a filter element including first and second end caps and a filter fastened between the end caps, and a sleeve. The sleeve is positioned around the filter and is joined to the first and second caps, thereby forming a single integral unit which is positioned within the housing. However, the filter decreases fluid hold-up waste, but does not promote air removal from the fluid.

A need thus exists for a blood filter that overcomes the disadvantages described above. In particular, there is a need in the art for a blood filter having a blood trap function and a filtering function, both of which assist in the removal of air and other particulates from the blood prior to being returned to the patient.

SUMMARY OF THE INVENTION

In light of the foregoing, one aspect of the present invention involves an arterial blood filter. The filter comprises an outer housing having a first section and a second section. The outer housing includes a blood inlet and blood outlet. A vent is formed in one section of the outer housing for discharging air. A filter element is disposed within the outer housing for filtering blood. An inner housing is disposed between the filter element and the outer housing. The inner housing extends substantially an entire length of the filter element and includes at least one opening at a bottom surface of the inner housing.

According to another aspect of the invention, a system for filtering blood is provided. The system includes a blood reservoir for connection to a vein of a patient, a pump for connection to the blood reservoir, an oxygenator for connection to the pump, and an arterial filter for connection to the oxygenator. The filter comprises an outer housing having a top section and a bottom section. The outer housing includes a blood inlet and blood outlet. A vent is formed in the top section of the outer housing for discharging air. A filter element is disposed within the outer housing for filtering blood. An inner housing is disposed between the filter element and the outer housing. The inner housing extends substantially an entire length of the filter element and includes at least one opening at a bottom surface of the inner housing.

Another aspect of the invention involves a blood filter for use in an extracorporeal circuit. The blood filter comprises an outer housing provided with a blood inlet for introducing blood into the outer housing and a blood outlet through which filtered blood exits the outer housing. A blood filter element is positioned within the outer housing to filter blood that has entered the outer housing through the blood inlet. The blood filter element surrounds an exterior space that is in communication with the blood outlet. An inner housing is positioned between the outer housing and the blood filter element and has an axial height at least equal to the axial height of said blood inlet.

BRIEF DESCRIPTION OF THE DRAWING FIGURES

Further features and characteristics of the present invention will become more apparent from the following detailed description considered with reference to the accompanying drawing figures in which like elements are designated by like reference numerals and wherein.

DETAILED DESCRIPTION OF THE INVENTION

The arterial blood filter according to the present invention is adapted to be used in connection with an extracorporeal circuit, which is used to filter blood during cardiac surgery. While the filter of the present invention is described in connection with filtering blood, it should be understood that it may be used to filter other body fluids such as plasma.

Figure 1:
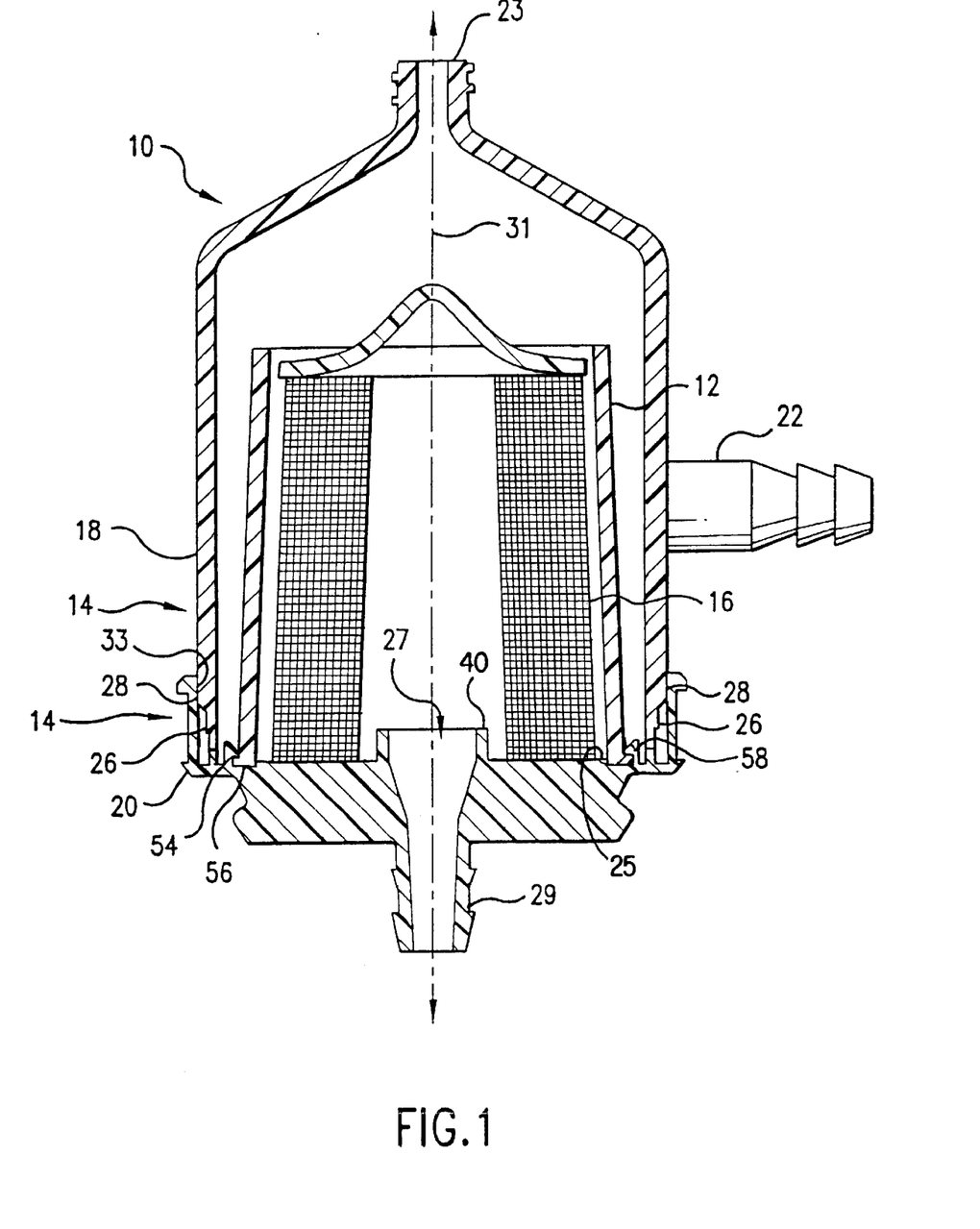
FIG. 1 is a vertical cross-sectional view of the filter according to the present invention.
Figure 4:
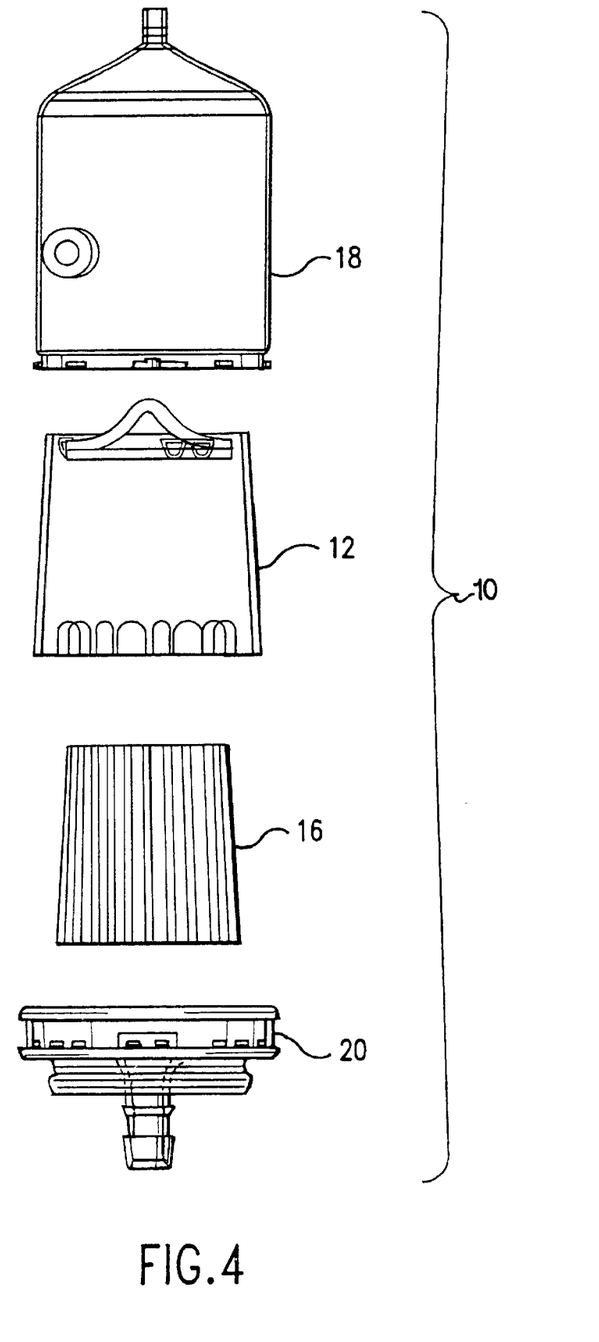
FIG. 4 is an exploded view of the filter according to the present invention.

With reference to FIGS. 1 and 4, the blood filter 10 of the present invention includes an inner housing 12 disposed between an outer housing 14 and a filter element 16. The inner housing 12 and the outer housing 14 may be formed of any desired synthetic resins including polycarbonate, polypropylene, polyethylene, styrene-butadiene (SB) resin, and methylene-butadiene styrene (MBS) resin. These components are preferably transparent to allow easy observation of the contents in the housing.

The outer housing 14 is preferably formed of two sections, a top section 18 and a bottom section 20 which are joined together with a liquid-tight seal after the inner housing 12 and the filter element 16 are inserted into the outer housing 14. Preferably, the upper portion of the top section 18 is shaped to be slightly dome-shaped or conical which serves as a containment field for the blood. An air vent 23 is provided at the uppermost portion of the top section 18 as shown in FIG. 1.

Figure 3:
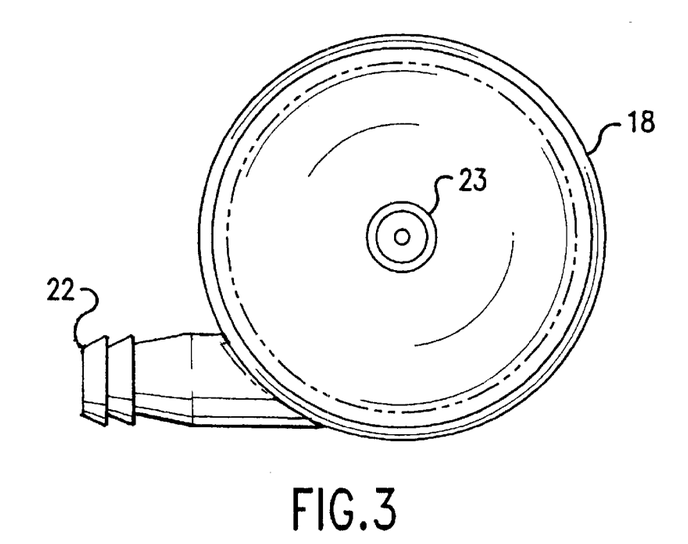
FIG. 3 is a top plan view of the top section of FIG. 2 according to the present invention.

The blood enters the top section 18 of the outer housing 14 via a blood inlet conduit 22 which is located oh the outer circumferential surface 28 of the top section 18. This blood inlet conduit 22 is oriented and positioned so that it protrudes along a line that is roughly tangential to the inner circumferential surface of the top section 18 of the outer housing 14. Stated differently, the central axis of the blood inlet conduit 22 is generally tangential to the inner circumferential surface of the top section 18 of the outer housing 14. This allows the blood flowing into the outer housing 14 through the blood inlet conduit 22 to form a swirling flow in one direction along the inner circumferential surface of the top section 18, as shown with reference to FIG. 3, to promote centripetal flow. Centripetal flow of the blood is advantageous in that it helps facilitate air removal. However, it should be understood that the central axis of the blood inlet conduit 22 may be positioned at other angles, and may be perpendicular to the inner circumferential surface of the top section 18 of the outer housing 14. In addition, the blood inlet conduit 22 may also be angled upward or downward. Advantageously, if the blood inlet conduit 22 is angled upward, more bubbles will be forced upwardly through the air vent 23 positioned at the upper end of top section 18 of the outer housing 14, thereby promoting more air removal. In contrast, if the conduit 22 is angled downward, the bubbles may be forced down through the filter material instead of flowing up and being purged out.

Preferably, the blood inlet conduit 22 is located about midway along the length of the top section 18 of the outer housing 14. This allows bubbles in the blood more time to rise and be purged prior to the blood entering the filter element 16. The inner diameter of the blood inlet conduit 22 should be preferably as large as possible to avoid an excessive pressure drop across the filter 10 and to minimize the shear forces as the blood enters the outer housing 14.

Figure 2:
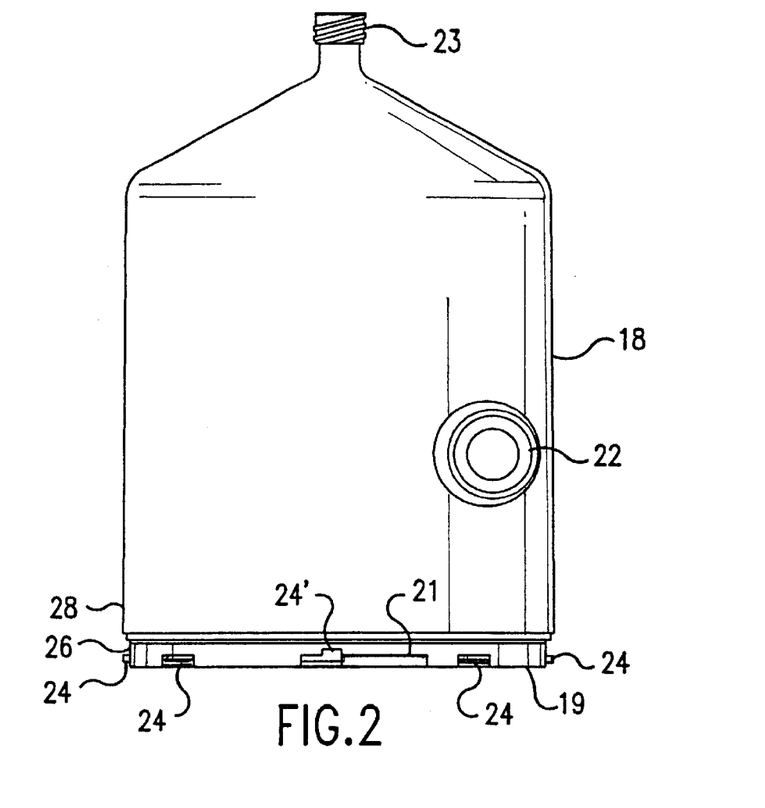
FIG. 2 is a perspective view of the top section of the outer housing of the filter according to the present invention.

With reference to FIGS. 1, 2, and 4, the inner and outer diameters of the top section 18 of the outer housing 14 gradually increase in the top to bottom direction, with the uppermost portion of the top section 18 of the outer housing 14 having a conical or funnel-like shape that points upwards. As mentioned above, an air vent 23 is provided as a protruding tip at the uppermost end of the top section 18 of the outer housing 14 for discharging gases that are produced when air bubbles are separated and removed from the blood being filtered. Further, although not specifically illustrated, the vent 23 is typically connected to a three-way stop cock for use therewith. As is well known in the art, a stop cock is a device that is attached to the luer port of the arterial filter i.e. the vent, and typically includes three valves. A first valve extends downwardly, and is connected to the air vent 23. A second valve extends upwardly from the first valve in the opposite direction, and is attached to a small diameter tube, which is known as a purge line for purging air from the arterial filter. The purged air and blood flow through this line to the cardiotomy reservoir. This line can be used to prime the arterial filter and is typically left open during a cardiopulmonary bypass procedure for continuous purging of the arterial filter, although it may be closed or opened as needed during the procedure. A third valve is positioned perpendicular to the first and second valves, and typically remains unused during the procedure.

With reference to FIG. 1, the bottom section 20 of the outer housing 14 is shaped to receive and be joined to the lower end of the top section 18 of the outer housing 14 by an adhesive, to thereby form an integrated, liquid tight outer housing 14. The upstanding wall of the bottom section 20 surrounds a surface 25 of the bottom section 20 that is substantially planar. The bottom section 20 of the outer housing 14 is provided with a blood outflowing section 27, the tip of which protrudes to form a blood outlet 29. Preferably, the blood outlet 29 and the vent 23 are aligned with the central axis 31 of the outer housing 14.

In order to assemble the top section 18 to the bottom section 20, adhesive is applied to the bottom section 20, and the top section 18 is placed on and sealed to the bottom section 20. However, in order to lock the top section 18 into a predetermined orientation with respect to the bottom section 20, and to prevent the top section 18 from rising in the adhesive, the top section 18 and the bottom section 20 include complementary elements forming an attachment mechanism. This attachment mechanism keeps the top section 18 fixed to the bottom section 20 during curing of the adhesive.

One part of the attachment mechanism involves protrusions 24 provided on the top section 18. As shown in FIG. 2, the protrusions 24 extend radially outwardly from the bottom portion of the outer surface of the top section 18 and are spaced apart from one another. Also, all of the protrusions 24 lie in a common plane. In the illustrated embodiment, there are eight protrusions 24, equally spaced about the bottom outer circumferential surface 26 of the top section 18, although more or less protrusions can be provided. Two of the eight protrusions are formed as L-shaped protrusions 24', only one of which is shown in FIG. 2. The two L-shaped portions 24' are located diametrically opposite one another at the bottom of the top section 18.

Figure 7:
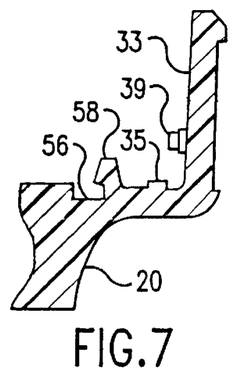
FIG. 7 is a cross sectional view of a portion of the bottom section of the outer housing according to the present invention.

As seen in FIG. 7, another part of the attachment mechanism involves a plurality of spaced apart ledges 39 disposed on the inner surface of the side wall 33 of the bottom section 20. The ledges 39 are directed radially inwardly and are equal in number to the number of protrusions 24 on the top section 18. Also, the ledges 39 are spaced apart at intervals equal to the interval of spacing between the protrusions 24 on the top section 18, and all of the ledges 39 lie in a common plane.

When the top section 18 is inserted into the bottom section 20 with the two sections disposed in a particular orientation relative to one another, the radially inwardly directed ledges 39 on the bottom section 20 are located relative to the radially outwardly directed protrusions 24 on the top section 18 such that when the top and bottom sections 18, 20 are rotated, the radially outwardly directed protrusions 24 on the top section 18 slide below the radially inwardly directed ledges 39 on the bottom section 20.

To facilitate proper orientation of the top and bottom sections 18, 20, the bottom end surface 19 of the top section 18 is provided with an elongated slot 21. The elongated slot 21 extends circumferentially along a portion of the bottom end surface 19 of the top section 18 from a point immediately adjacent one of the L-shaped protrusions 24'. As can be seen from FIG. 2, the bottommost part of the outer circumferential surface 26 of the top section 18 is also slightly recessed radially inwardly, from the remainder of the outer surface 28 of the top section 18 to allow for the adhesive to enter between the recessed bottommost part of the top section 18 and the bottom section 20.

To further aid in the proper assembly of the top and bottom sections 18, 20, the bottom section 20 is preferably provided with a plurality of axially upwardly extending raised sections 35. These raised sections 35 are spaced apart from one another and are located along a circle having a diameter that is substantially equal to the diameter of the bottom end surface 19 of the top section 18. This means that when the top section 18 is inserted into and properly oriented with respect to the bottom section 20, the bottom end surface of the top section 18 rests or sits on the raised sections 35.

Figure 8:
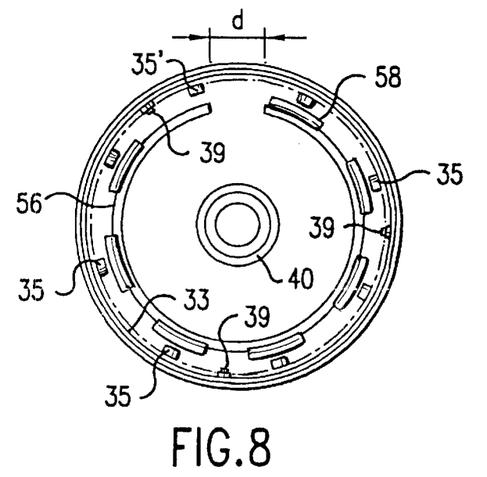
FIG. 8 is a top plan view of the bottom section of the filter according to the present invention.

As shown in FIG. 8, the raised sections 35 are positioned between adjacent pairs of the ledges 39 with respect to the circumferential direction. The raised sections 35 provide gaps between the top section 18 and the bottom section 20 for adhesive, thus providing a stronger bond between the top section 18 and the bottom section 20. All but one of the raised sections 35 possess the same height, with the remaining raised section 35' possessing a height that is greater than the height of the other raised sections 35.

During assembly, the top section 18 is placed on the bottom section 20 such that the raised section 35' having the greatest height is received in the slot 21 in the bottom end surface 19 of the top section 18. When the raised section 35' possessing the greatest height is received in the slot 21 in the bottom end surface 19 of the top section 18, and upon rotating the top and bottom sections 18, 20 relative to one another, the radially outwardly directed protrusions 24 on the top section 18 are able to slide below the radially inwardly directed ledges 39 on the bottom section 20, thereby causing the top and bottom sections 18, 20 to be secured together. The protrusions 24 are able to slide below the ledges 39 because when the raised section 35' possessing the greatest height is received in the slot 21, the relative axial positioning of the top and bottom sections 18, 20 is such that the plane in which the radially outwardly directed protrusions 24 lie is disposed below the plane in which the radially inwardly directed ledges 39 lie. The positioning of the highest raised section 35' within the slot 21 in the bottom end surface 19 of the top section 18 allows the top and bottom sections 18, 20 to be secured together relative to one another in one and only one manner that defines a specific relative orientation between the two sections 18, 20.

The top and bottom sections 18, 20 are unable to be secured togther in other relative orientations because when the raised section 35' possessing the greatest height is not positioned within the slot 21, the bottom end surface 19 of the top section 18 rests on the raised section 35' possessing the greatest height. In this situation, the relative axial positioning of the top and bottom sections 18, 20 is such that the plane in which the radially outwardly directed protrusions 24 lie is coplanar with the plane in which the radially inwardly directed ledges 39 lie. Thus, when the top and bottom sections 18, 20 are rotated in this situation, the radially outwardly directed protrusions 24 on the top section 18 contact the radially inwardly directed ledges 39 on the bottom section 20 and are not properly positioned to slide below the radially inwardly directed ledges 39.

As mentioned above, once the raised section 35' possessing the greatest height is received in the slot 21, the top section 18 can be axially positioned relative to the bottom section 20 in such a manner that, upon rotating the two sections 18, 20, the radially outwardly directed protrusions 24 on the top section 18 are able to slide below the radially inwardly directed ledges 39 on the bottom section 20. The two sections 18, 20 can be rotated relative to one another until the upper leg of the two L-shaped protrusions 24' abut against respective side wall ledges 39 on the bottom section 20. When the radially outwardly directed protrusions 24 on the top section 18 slide below the radially inwardly directed ledges 39 on the bottom section 20, the top and bottom section 18, 20 are axially fixed relative to one another. Thus, these respective attachment portions prevent the top section 18 from rising in the adhesive during curing. That is, the top and bottom sections do not move relative to one another during curing of the adhesive. It should be recognized that the top section 18 and the bottom section 20 may include other features to aid in proper assembly of the outer housing 14. For instance, the top section 18 and the bottom section 20 may include assembly features similar to those described in U.S. Pat. No. 5,618,425, to Mitamura et al., the entire disclosure of which is incorporated herein by reference.

The filter element 16 is located inside the inner housing 12 for filtering air bubbles and foreign substances that have been mixed with the blood, as shown with reference to FIGS. 1 and 4. The filter element 16 may be comprised of materials that are acceptable for contact with blood and provide adequate filtration.

Preferably, the filter element 16 is comprised of three layers of material. The innermost and the outermost layers are fabricated from the same material and provide support, with the pore size of the filter material preferably being between about 200–1500 $\mu$m. However, it should be understood that the innermost and outermost layers may be fabricated from material having different pore sizes. The middle layer should be made from a finer material for filtration, that is material that is capable of filtering out smaller particles than the other layers. In the preferred embodiment, the middle layer is made from a polyester woven material, with the pore size of the filter material being between about 20–40 $\mu$m.

The filter element 16 is pleated, cut, and welded into the appropriate size, preferably, a conical shape (i.e., the outer diameter of the filter element decreases from the bottom to the top). This shape helps reduce the priming volume and makes the whole blood filter 10 easier to prime. A filter element 16 that may be used in the blood filter of the present invention is described in U.S. Pat. No. 5,618,425. However, a cylindrical shaped filter element may also be used.

Figure 5:
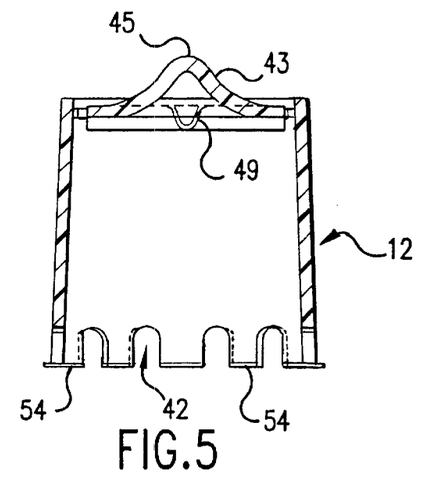
FIG. 5 is a cross sectional view of the inner housing of the filter according to the present invention.
Figure 6:
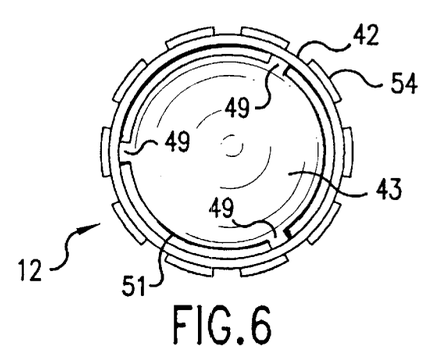
FIG. 6 is a bottom plan view of the inner housing of FIG. 5 according to the present invention.

With reference to FIGS. 1, 5, and 6, the inner housing 12 is disposed between the outer housing 14 and the filter element 16. The inner housing 12 possesses a generally cylindrical shape, and extends the entire length of the filter element 16. Preferably, the outer diameter of the inner housing 12 decreases in a direction from the bottom to the top. The inner housing 12 functions to hold and support the filter element 16. In addition, the inner housing 12 functions to promote gentle flow of the blood, and to regulate the pressure drop within the filter 10. Instead of the fluid coming in direct contact with the filter element 16 at high shear rates, the flow of the blood entering the filter is reduced by the inner housing 12.

The inner housing 12 has openings at both its top and bottom for the inflow of fluid. With reference to FIGS. 5 and 6, a plurality of openings 42 are disposed along the bottom outer circumferential surface of the inner housing 12. Preferably, the openings 42 consecutively and gradually increase in size from smallest to largest, with the smallest opening being positioned such that it is substantially closest to the blood inlet conduit 22 with respect to the circumferential direction of inflowing blood. That is, the smallest opening is positioned almost directly below the point at which the blood inlet conduit 22 opens into the interior of the housing.

The smallest opening 42 is located closest to the blood inlet conduit 22 with respect to the direction of blood inflow because the area around the blood inlet conduit 22 is a high pressure area. Also, the largest opening 42 is located furthest from the blood inlet conduit 22 with respect to the direction of blood inflow. By having the largest opening located away from the blood inlet conduit 22 with respect to the direction of blood inflow, the pressure between the inner housing and the outer housing decreases as the fluid flows around the housing. In addition, if large amounts of air enter the arterial filter from the oxygenator, the majority of the air is able to flow up toward the top of the housing and not directly to the filter element 16. By having the smaller openings nearer the blood inlet conduit 22, this helps prevent air from going directly into the filter element 16. The advantage of increasing the size of the holes at the bottom of the inner housing 12 is to regulate the pressure drop.

In the preferred embodiment, there are ten U-shaped openings 42 with the height of the openings 42 being substantially the same and the width of the openings 42 at the bottom increasing in size from approximately 3 mm to 12 mm. However, a different number of openings may be provided and the openings 42 may be of a different size than that mentioned above, preferably so long as there is substantially an equal pressure drop across the filter 16 itself.

Also, if the area of the openings 42 at the bottom is not sufficient, blood may not be able to drain from the bottom. As a result, blood contained between the inner housing 12 and the outer housing 14 may drip over the side of the inner housing 12, possibly creating bubbles such as when the inner housing 12 is less than full. Thus, the area of the openings 42 at the bottom should be selected to avoid such an occurrence. Preferably, the combined surface area of the openings 42 is greater than 2 cm$^2$.

The inner housing 12 also has openings 51 at its top through which a majority of the blood flows. Preferably, the openings 51 are defined between the inner housing 12 and a filter cap 43 which is attached to the top of the filter element 16 and holds the top of the filter element 16 in place, thereby inhibiting or preventing the filter element 16 from collapsing due to clotting or high flow rates. The cap 43 is generally conically shaped with a peak at its center 45 which assists in air removal by directing the vortex created by the centripetal flow motion to the middle of the top section 18 of the outer housing 14 and out through the vent 23.

The cap 43 is preferably circular in shape and is affixed to the top surface of the filter element 16 by adhesive. Polyurethane is a preferred adhesive but others can also be used. In the preferred form of the invention, the cap 43 and the inner housing 12 are integrally formed in one piece as a unitary structure. The cap 43 and the inner housing 12 can be molded together and are formed to provide the plurality of openings 51, with adjacent pairs of openings 51 being separated by connecting ribs 49. The openings 51, which are illustrated as being three in number but which can be a greater or lesser number, are designed to allow blood to flow into the interior of the inner housing 12. The cap 43 and the inner housing 12 may define, for example, three arcuate openings 51 for the flow of blood, with each arcuate opening being located between adjacent pairs of ribs 49. The combined surface area of the openings 51 is preferably greater than 2.0 cm$^2$. Also, it is possible to fabricate the cap 43 and the inner housing 12 separately and to then connect the two together in a way that provides the openings 51.

The inner housing 12 allows for additional bolus air removal. If a large amount of air is introduced into the filter 10, the fluid volume within the filter 10 will decrease. If the fluid volume decreases below the top level of the openings 51, fluid can still enter the filter element 16 through the bottom openings 42. Moreover, as the blood flows through the blood inlet conduit 22, instead of the blood coming in direct contact with the filter element 16, the blood comes in contact with the outer wall of the inner housing 12. In addition, centripetal flow is improved, while more time is provided before the bubble point of the material is reached.

To affix the inner housing 12 to the outer housing 14, the lower circumferential surface 54 of the inner housing 12 protrudes outwardly slightly in the radial direction and is received in an annular groove 56 disposed in the bottom section 20 of the outer housing 14, as shown with reference to FIGS. 1, 5, 7, and 8. Preferably, the groove 56 extends a little less than 360°, with the distance d between the adjacent ends of the groove 56 as shown in FIG. 8 being approximately equal to the width of the largest opening 42 of the inner housing 12. This allows the inner housing 12 to be placed in only one orientation relative to the bottom section 20 to thereby strategically align the smallest opening with the blood inlet conduit 22. That is, as mentioned above, the engagement between the highest raised section 35' and the slot 21 ensures that the top section 18 of the outer housing is positioned in one particular orientation with respect to the bottom section 20 of the outer housing 14. The way in which the largest opening 42 of the inner housing 12 straddles the distance d between the ends of the groove 56 ensures that the inner housing 12 is positioned in one particular orientation with respect to the bottom section 20 of the outer housing 14. As a result, the inner housing 12 is positioned relative to the top section 18 of the outer housing 14 so that the smallest opening 42 in the bottom of the inner housing 12 is located closest to the blood inlet conduit 22 with respect to the circumferential or blood inflow direction.

Disposed along the outer edge of the groove 56 are preferably a plurality of inwardly directed ribs 58 for engaging (e.g., snap locking) and holding the inner housing 12 in place. In the preferred embodiment, there are seven ribs 58 disposed about the annular groove 56, as shown with reference to FIG. 8. The ribs 58 are designed to engage the outwardly protruding lower surface 54 of the inner housing 12. The inner housing 12 with the filter element 16 are permanently attached to the bottom section 20 by an adhesive, RF heating, or the like. Preferably, polyurethane is the adhesive used. The ribs 58 prevent the inner housing 12 from rising in the polyurethane during curing.

To assemble the blood filter 10, adhesive is applied to the planar top surface of the bottom section 20. The inner housing 12 is pressed into the adhesive filled groove 56 in the specific orientation, while the filter element 16 is attached to the planar surface 25 of the bottom section 20. To prevent the adhesive from flowing into the outlet conduit 29, the blood outflow section 27 includes a raised annular portion 40 as seen with reference to FIGS. 1 and 8. The outer diameter of the raised annular portion 40 is smaller than the inner diameter of the filter element 16.

Once the inner housing 12 is locked into place relative to the bottom section 20, the top section 18 is placed on the bottom section 20, and it then rotated and locked in place in the manner described above. The bottom end of the top section is thus placed in the adhesive. Once the filter 10 is assembled, the filter 10 may be integrated as part of an extracorporeal circuit for treatment of blood as disclosed in U.S. Pat. No. 5,618,425.

Figure 9:
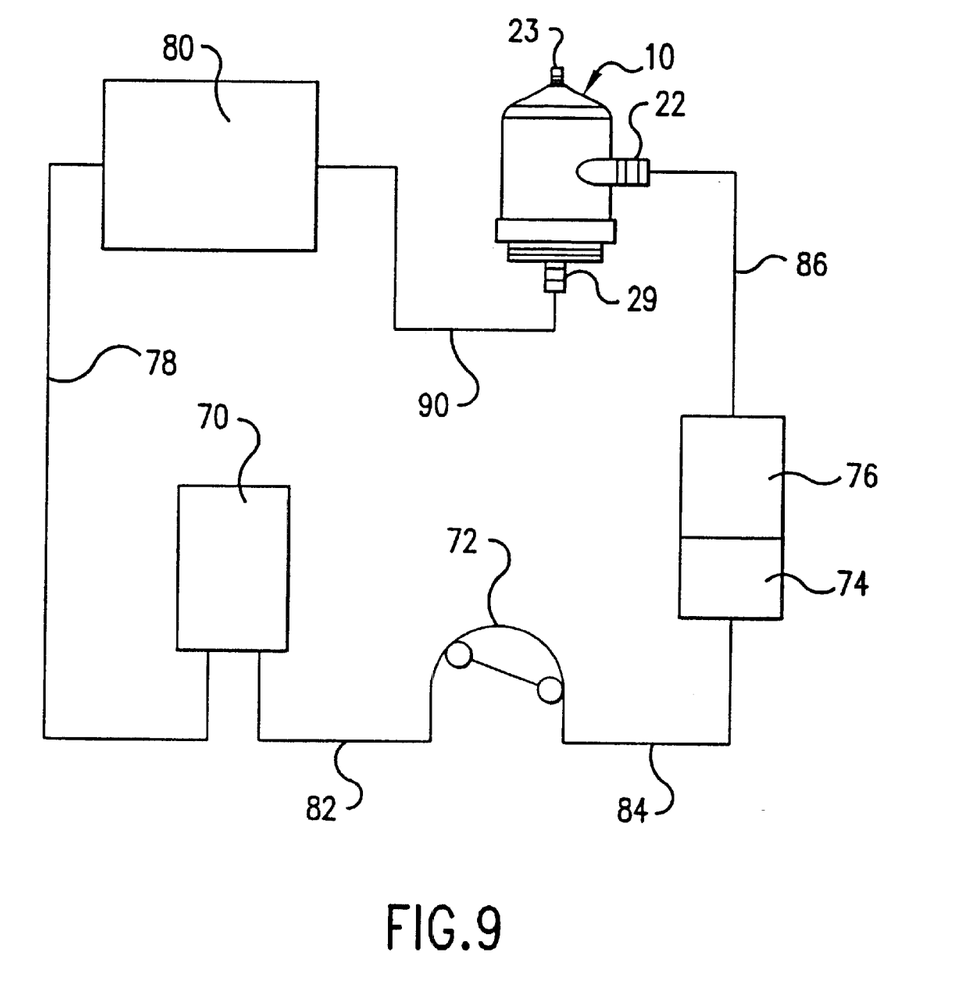
FIG. 9 illustrates a blood treatment system incorporating the filter of the present invention.

With reference to FIG. 9, the extracorporeal circuit may include a blood reservoir 70, a roller pump 72, a heat exchanger 74, an oxygenator 76, and the filter 10 according to the present invention. A first tube 78 connects a vein of a patient 80 to the blood reservoir 70. A second tube 82 connects the blood reservoir 70 to the roller pump 72. A third tube 84 connects the roller pump 72 to the heat exchanger 74. A fourth tube 86 connects the oxygenator 76 to the inlet conduit 22 of the filter 10. A fifth tube 90 connects the outlet conduit to the artery of the patient, typically the aorta.

Blood taken from the vein of a patient 80 is transferred from the first tube 78 to the blood reservoir 70. The roller pump 72 is then actuated to transfer the blood through the second tube 82 and the third tube 84, to the heat exchanger 74. Upon exiting the heat exchanger 74, the blood flows into the oxygenator 76, where the blood is oxygenated and carbon dioxide contained therein is removed.

The blood then flows through the fourth tube 86, and enters the filter 10 through the inlet conduit 22. The inlet conduit 22 is positioned in a manner to direct the flow in a circular manner to aid in the removal of any air that is mixed with the blood. The blood flows around the inner housing 12 with some blood entering the filter element through the openings 59 located in the top of the inner housing 12, and some blood entering through the bottom openings 42. The flow is directed to the top due to centripetal forces created by the location of the inlet conduit 22. In the case where the blood is mixed with bubbles, buoyancy forces these bubbles to float up towards the top section 18 while they move in a swirling motion. Upon reaching the vent 23, the bubbles are discharged to the outside of the filter 10.

It is to be noted that the use of the apparatus according to the present invention is not limited to the blood filter as shown in the Figures, and can be utilized for other medical purposes.

EXAMPLE

An exemplary embodiment of a filter according to the present invention can have dimensions along the order discussed below. It is to be understood that the present invention is defined by the appended claims and not the specific details of this Example.

| | |
|---|---|
| Inside diameter of the blood inlet: | 9.30 mm |
| Inside diameter of the blood outlet: | 9.30 mm |

| | |
|---|---|
| Inside diameter of the vent: | 4.32 mm |
| Outer diameter of the top section of the outer housing: | 66.77 mm |
| Height of the top section of the outer housing: | 95.11 mm |
| Outer diameter of the bottom section of the outer housing: | 72.00 mm |
| Diameter of the annular groove in the bottom section of the outer housing: | 56.00 mm |
| Distance from bottom of the top section to blood inlet conduit: | 35.00 mm |
| Diameter of the filter cap: | 45.80 mm |
| Outer diameter of the filter element: | 44.40 mm |
| Height of the inner housing: | 65.00 mm |
| Height of the openings in the inner housing: | 10.00 mm |
| Diameter of the inner housing: | 53.90 mm |

The inner housing 12 of the filter 10 according to the present invention provides for non turbulent flow of the blood through the filter element 16. By providing a barrier between the outer housing 14 and the filter element 16, the fluid will not come in direct contact with the filter element 16, but will come into contact with the outer wall of the inner housing 12. Thus, instead of the fluid coming in direct contact with the filter element 16 at high shear rates, the flow of the blood entering the filter element 16 is reduced by the openings located at the top and bottom of the inner housing 12. Therefore, the flow of the fluid that passes through the filter element 16 is gentle. The inner housing 12 also advantageously provides support for the filter element 16, preventing the filter element 16 from collapsing and blocking the blood outlet 29.

The principles, preferred embodiment and manner of use of the present invention have been described in the foregoing specification. However, the invention which is intended to be protected is not to be construed as limited to the particular embodiment described. Further, the embodiment described herein is to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the invention be embraced thereby.

What is claimed is:

1. An arterial blood filter, comprising:
   an outer housing having a first section and a second section, said outer housing including a blood inlet and blood outlet;
   a vent formed in one of said first and second sections of said outer housing for discharging air;
   a filter element disposed within said outer housing for filtering blood; and
   an inner housing disposed between said filter element and said outer housing, said inner housing extending substantially an entire length of said filter element and including at least one opening at a bottom portion of a side surface of said inner housing to permit blood flow into the inner housing from outside the inner housing by way of the at least one opening.

2. The arterial filter of claim 1, wherein the at least one opening at the bottom portion of the side surface of said inner housing includes a plurality of openings disposed at the bottom portion of the side surface of said inner housing.

3. The arterial filter of claim 2, wherein said openings increase in size along a circumference of said inner housing.

4. The arterial filter of claim 3, wherein a smallest of said openings is disposed circumferentially closest to said blood inlet.

5. The arterial filter of claim 3, wherein said openings possess substantially the same height.

6. The arterial filter of claim 2, wherein a combined surface area of said openings is greater than 2.0 cm$^2$.

7. The arterial filter of claim 1, wherein said vent is formed in said first section, and said second section includes means for rotationally locating said inner housing in one position relative to the second section.

8. The arterial filter of claim 7, wherein said first section is a top section and said second section is a bottom section, said bottom section of said outer housing including an annular groove that receives and supports a bottom portion of said inner housing.

9. The arterial filter of claim 1, wherein said blood inlet is tangentially disposed substantially midway along a side wall of said top section of said outer housing for introducing blood into the filter, and said blood outlet is disposed in a center portion of said second section of said outer housing.

10. The arterial filter of claim 1, wherein said inner housing is formed separately from said outer housing.

11. The arterial filter of claim 1, further comprising a filter cap disposed on a top portion of said filter element and rigidly connected to said inner housing, and including at least one opening provided between said filter cap and said inner housing.

12. The arterial filter of claim 1, wherein a bottom portion of said inner housing is glued to said second section of said outer housing.

13. The arterial filter of claim 1, wherein said first section is a top section and said second section is a bottom section, said filter element including a hole extending along the axial extent of the filter element, said hole defining an inner diameter of the filter element, said bottom section of said outer housing including a raised first annular portion centrally disposed adjacent said outlet conduit, said first annular portion having a diameter that is smaller than the inner diameter of said filter element.

14. The arterial filter of claim 1, wherein said filter element and said inner housing each have an outer diameter that increases from top to bottom.

15. The arterial filter of claim 1, wherein the side surface of the inner housing is an upstanding side surface located radially outwardly of the filter element.

16. A system for processing blood, comprising:
    a blood reservoir for connection to a vein of a patient;
    a pump for connection to said blood reservoir;
    an oxygenator for connection to said pump; and
    an arterial filter for connection to said oxygenator, said arterial filter comprising an outer housing having a top section and a bottom section, said outer housing including a blood inlet and blood outlet;
    a vent formed in said top section of said outer housing for discharging air;
    a filter element disposed within said outer housing for filtering blood; and
    an inner housing disposed between said filter element and said outer housing, said inner housing extending substantially an entire length of said filter element and including at least one opening at a bottom portion of a side surface of said inner housing to permit blood flow into the inner housing from outside the inner housing by way of the at least one opening.

17. The system of claim 16, wherein said blood inlet is tangentially disposed substantially midway along a side wall of said top section of said outer housing for introducing blood into the filter, and said blood outlet is disposed in a center portion of said bottom section of said outer housing.

18. The system of claim 16, further comprising a filter cap disposed on a top portion of said filter element and fixed to said inner housing, and including at least one opening provided between said filter cap and said inner housing.

19. The system of claim 16, wherein said filter cap is glued to a top portion of said filter element, and a bottom portion of said filter element is glued to said bottom section of said outer housing.

20. The system of claim 16, wherein said bottom section of said outer housing includes a raised annular portion centrally disposed adjacent said outlet conduit, said annular portion having an outer diameter that is smaller than an inner diameter of said filter element.

21. The system of claim 16, wherein the at least one opening at the bottom portion of the side surface of said inner housing includes a plurality of openings disposed at the bottom portion of the side surface of said inner housing.

22. The system of claim 21, wherein said openings increase in size along a circumference of said inner housing.

23. The system of claim 16, wherein the side surface of the inner housing is an upstanding side surface located radially outwardly of the filter element.

24. A blood filter for use in an extracorporeal circuit, comprising:
   an outer housing provided with a blood inlet for introducing blood into the outer housing and a blood outlet through which filtered blood exits the outer housing;
   a blood filter element positioned within the outer housing to filter blood that has entered the outer housing through the blood inlet, the blood filter element surrounding an exterior space that is in communication with the blood outlet;
   an inner housing positioned between the outer housing and the blood filter element, said inner housing having an axial height at least equal to the axial height of said blood inlet; and
   at least one opening formed at a bottom portion of a side surface of the inner housing to permit blood flow into the inner housing from outside the inner housing by way of the at least one opening.

25. The blood filter of claim 24, wherein the at least one opening at the bottom portion of the side surface of said inner housing includes a plurality of openings disposed at the bottom portion of the side surface of said inner housing.

26. The blood filter of claim 25, wherein said openings increase in size along a circumference of said inner housing.

27. The blood filter of claim 24, wherein said inner housing is formed separately from said outer housing.

28. The blood filter of claim 24, further comprising a filter cap disposed on a top portion of said blood filter element and fixed to said inner housing, and including at least one opening provided between said filter cap and said inner housing.

29. The blood filter of claim 24, wherein said blood filter element includes a hole extending along the axial extent of said blood filter element, said hole defining an inner diameter of said filter element, said outer housing including a bottom section provided with a raised first annular portion centrally disposed adjacent said outlet conduit, said first annular portion having a diameter that is smaller than the inner diameter of said filter element.

30. The blood filter of claim 24, wherein the side surface of the inner housing is an upstanding side surface located radially outwardly of the blood filter element.

* * * * *